United States Patent [19]

Bastie et al.

[11] Patent Number: 5,193,104
[45] Date of Patent: Mar. 9, 1993

[54] METHOD FOR ANALYZING MONOCRYSTALLINE PARTS BY X-RAYS

[75] Inventors: Pierre Bastie, Corenc; Bernard Hamelin, Seyssinet, both of France

[73] Assignee: Centre National de la Recherche Scientifique, Paris, France

[21] Appl. No.: 779,191

[22] Filed: Oct. 22, 1991

[30] Foreign Application Priority Data

Oct. 23, 1990 [FR] France .................. 90 13330

[51] Int. Cl.[5] .................................. G01N 23/207
[52] U.S. Cl. ..................................... 378/73; 378/70; 378/71; 378/84; 378/87; 378/161; 378/145; 378/147; 378/58; 378/62; 250/308; 250/307
[58] Field of Search .............. 378/73, 58, 74, 147, 378/70, 72, 145, 87, 161, 84, 62; 250/206, 306, 307, 308, 399, 310

[56] References Cited

U.S. PATENT DOCUMENTS

| | | | |
|---|---|---|---|
| 3,833,810 | 9/1974 | Efanov et al. | 378/74 |
| 4,959,548 | 9/1990 | Kupperman et al. | 378/72 |
| 5,016,266 | 5/1991 | Meurtin | 378/73 |
| 5,093,573 | 3/1992 | Mikoshiba et al. | 250/310 |
| 5,136,624 | 8/1992 | Schneider et al. | 378/73 |

FOREIGN PATENT DOCUMENTS 488180 1/1969 Switzerland.

OTHER PUBLICATIONS

Industrial Laboratory, vol. 45, No. 6, Jun. 1979, "Topographic X-Ray Camera", L. G. Shabel'Nikov, pp. 676-677.

Aristov et al., "Role of Entrance Slit in the X-Ray Section Topography of Single Crystals" *Physica Status Solidi (a)*, vol. 62, No. 2 (Dec. 1980), pp. 431-440.

T. Kojima et al., "X-Ray Diffraction Microscopy of an Electronic Streak Camera System", *Japanese Journal of Applied Physics*, vol. 27, No. 7 (Jul. 1988), pp. 1331-1334.

Compagnie Francaise Thomson Houston-Hotchkiss Brandt, CH-A-488180.

*Primary Examiner*—Constantine Hannaher
*Assistant Examiner*—Kim-Kwok Chu
*Attorney, Agent, or Firm*—Lowe, Price, LeBlanc & Becker

[57] ABSTRACT

An X-ray volume analysis method of crystalline defects of a part (11), comprises the steps of positioning the part in the plane situated at equal distance from the focus of an X-ray source and a focusing plane (14); illuminating the part from a punctual X-ray source (10) by a beam of a large spectral width $\Delta\lambda$ and of determined angular opening $\Delta\theta$, the opening $\Delta\theta$ of the beam being fixed by $\Delta\theta \leq \Delta\lambda/2d.\cos\theta$, d being the interreticular distance for the considered reticular planes; orienting the part (11) to obtain the diffraction on a chosen family of reticular planes (30); and collecting and analyzing the X-ray beam near the focusing plane or beyond.

17 Claims, 5 Drawing Sheets

METHOD FOR ANALYZING MONOCRYSTALLINE PARTS BY X-RAYS

BACKGROUND OF THE INVENTION

The present invention relates to a volume analysis method of the crystallographic quality of monocrystalline parts by high energy X-rays.

This technique is particularly useful for the analysis of monocrystalline turbine blades, which bear very high stresses and must hence be free from defects.

This technique is also useful in the field of crystalline growth (electronic industry, research, ...) where it is desired to control, in real time and through the walls of an oven, the quality of the materials during growth.

The various known methods for analyzing such materials by X-rays only provide surface information which is often punctual. Moreover, the known volume methods use diffractometers needing the use of a monochromatic beam often difficult to use in industrial environment (radioactive sources, synchrotron radiation ...).

The present invention uses the known effect of refocusing of a polychromatic X-ray beam illuminating a monocrystalline surface.

SUMMARY OF THE INVENTION

More particularly, the present invention provides an X-ray volume analysis method of crystalline defects of a part, comprising the steps of positioning the part in the plane situated at equal distance from the focus of an X-ray source and a focusing plane; illuminating the part from a punctual X-ray source by a beam of a large spectral width $\Delta\lambda$ and of determined angular opening $\Delta\theta$, the opening $\Delta\theta$ of the beam being fixed by $\Delta\theta \leq \Delta\lambda/2d\cdot\cos\theta$, d being the interreticular distance for the considered reticular planes; orienting the part to obtain the diffraction on a chosen family of reticular planes; and collecting and analyzing the X-ray beam rear the focusing plane or beyond.

According to an embodiment of the invention, the analysis of the image comprises the steps of isolating by diaphragms the observed spots in the focusing plane; collecting and analyzing the images transmitted beyond the focusing plane.

According to an embodiment of the invention, the beam comes from a punctual focus and is diaphragmed by an opening placed between the X-ray source and the part so that the beam substantially illuminates the whole part.

According to an embodiment of the invention, the X-ray generator is a source providing a radiation of an energy greater than 100 keV, having a large spectral width.

According to an embodiment of the invention, the part is a monocrystal, for example a turbine blade.

Thanks to this method, it is possible to:
directly determine if the whole illuminated structure is monocrystalline or not;
define the orientation of the crystallographic axes;
quantify the quality of the crystal ("mosaic degree");
localize and visualize the eventual crystalline defects;
visualize purely structural defects (lack of material, bubbles, ...) by observing the non diffracted beam (radiography);
obtain a variable enlargement of the observed images.

BRIEF DESCRIPTION OF THE DRAWINGS

The foregoing and other objects, features and advantages of the present invention will be described in more detail in the following description of preferred embodiments by referring to the attached drawings in which:

FIG. 2b is a projection view of the assembly of FIG. 2a;

DETAILED DESCRIPTION OF THE PREFERRED EMBODIMENTS

The present invention uses a micro focus high energy X-ray generator (100–500 keV), the spectrum of which is essentially comprised of the braking radiation, i.e., bremsstrahlung electromagnetic radiation that is emitted by an electrical particle accelerated in its collision with the nucleus of an atom. These generators are often used since the last years for radiography applications. The normalized spectrum of such generators is shown in FIG. 1 in which the vertical coordinates correspond to the normalized intensity, and horizontal coordinates to the wave length in Angströms (1 Å=0.1 nm).

Figure 1:
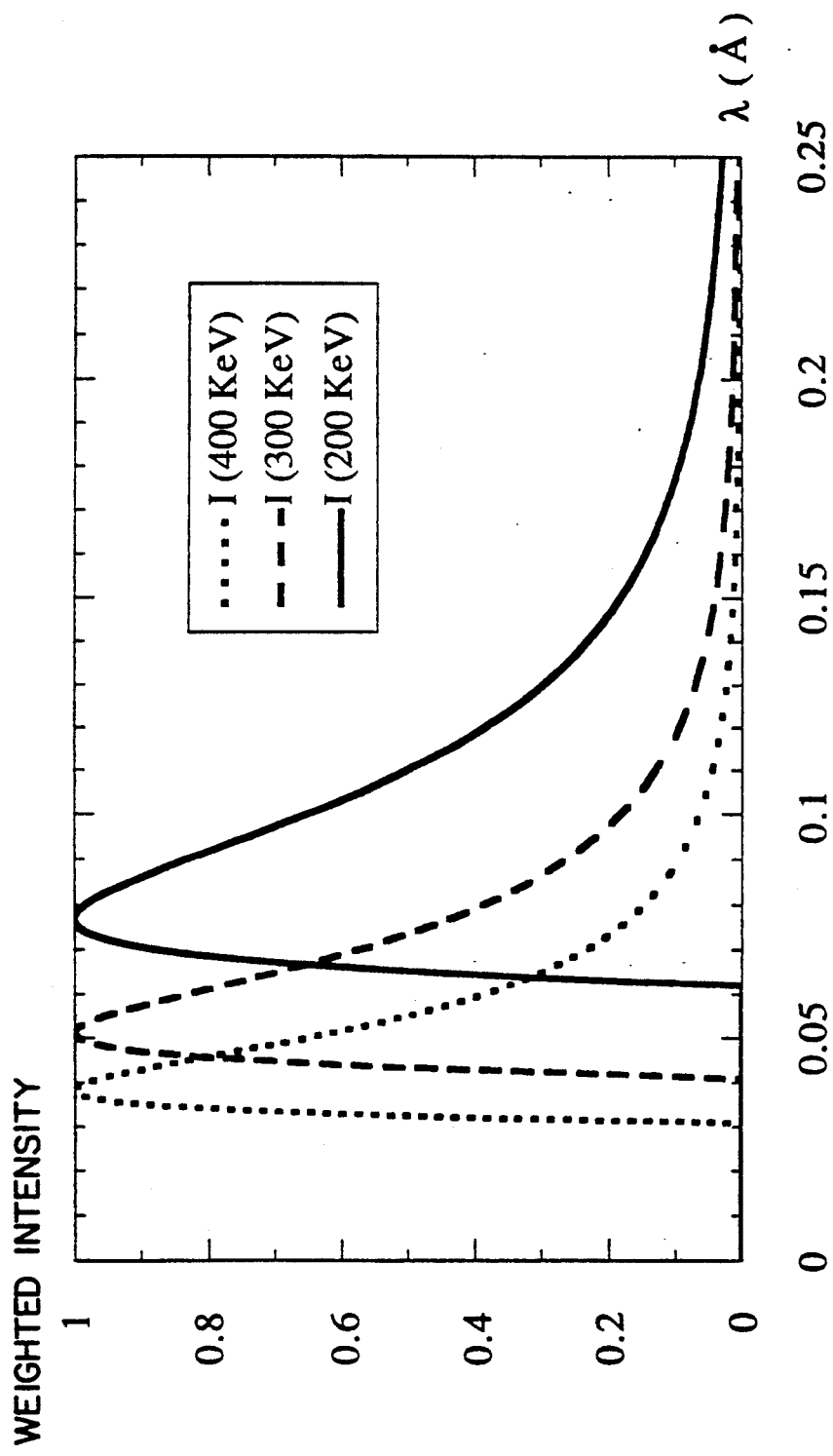
FIG. 1 shows the X-ray spectrum of an X-ray source used according to the invention.

In FIG. 1, curves 1, 2 and 3 correspond respectively to high voltages E of the generator of 400, 300 and 200 keV. As it is known, the cut-off wave length $\lambda_m$ (minimum wave length or maximum energy) has a value of $\lambda_m = 12.4/E$, E being expressed in keV. The range of emitted wave lengths hence varies approximately (width at half height) from 0.03 to 0.12 Å for an energy of 400 keV and from 0.07 to 0.12 Å for an energy of 200 keV.

Figure 2A:
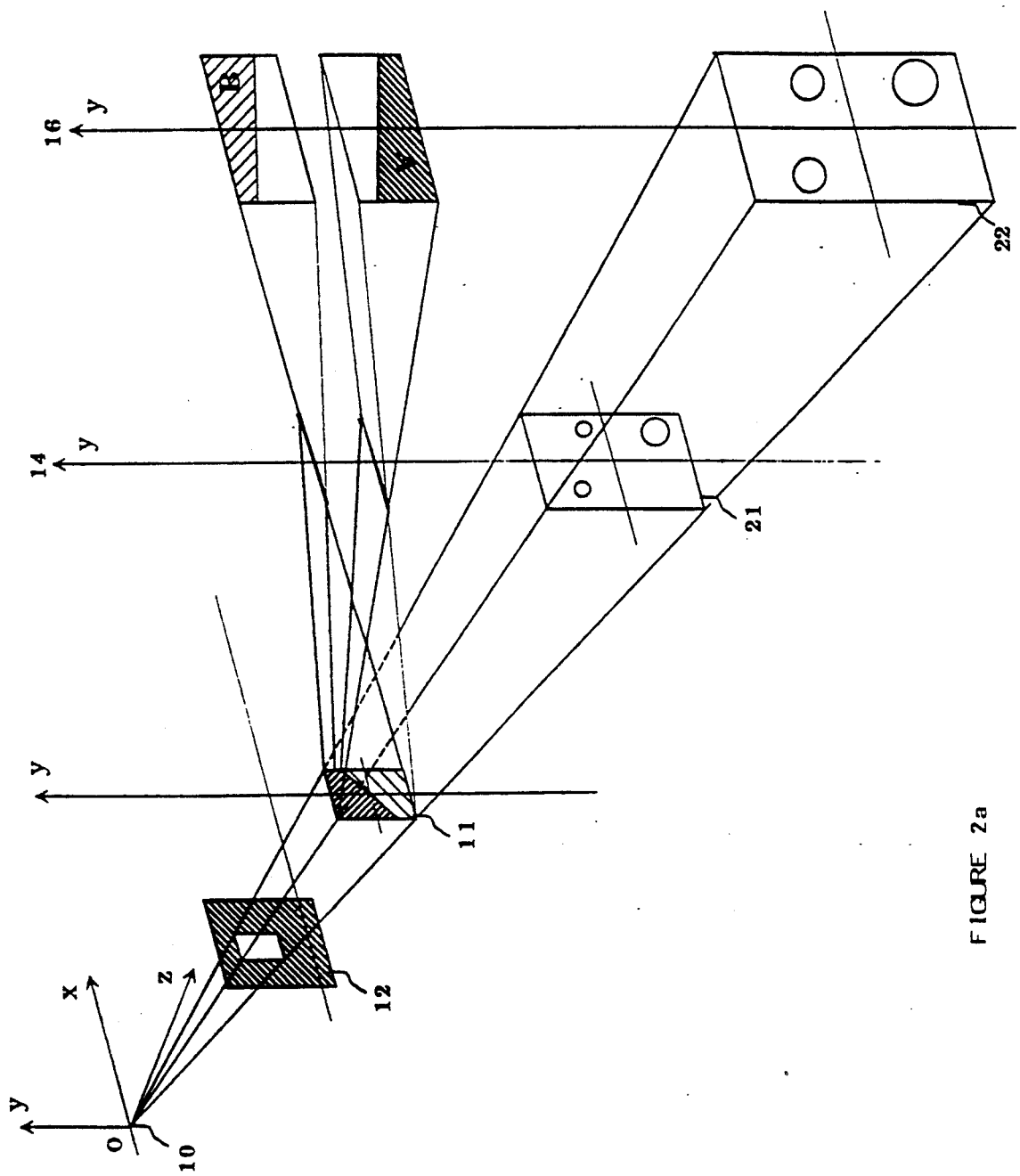
FIG. 2a is a schematic diagram of the X-ray analysis assembly according to the invention.
Figure 2B:
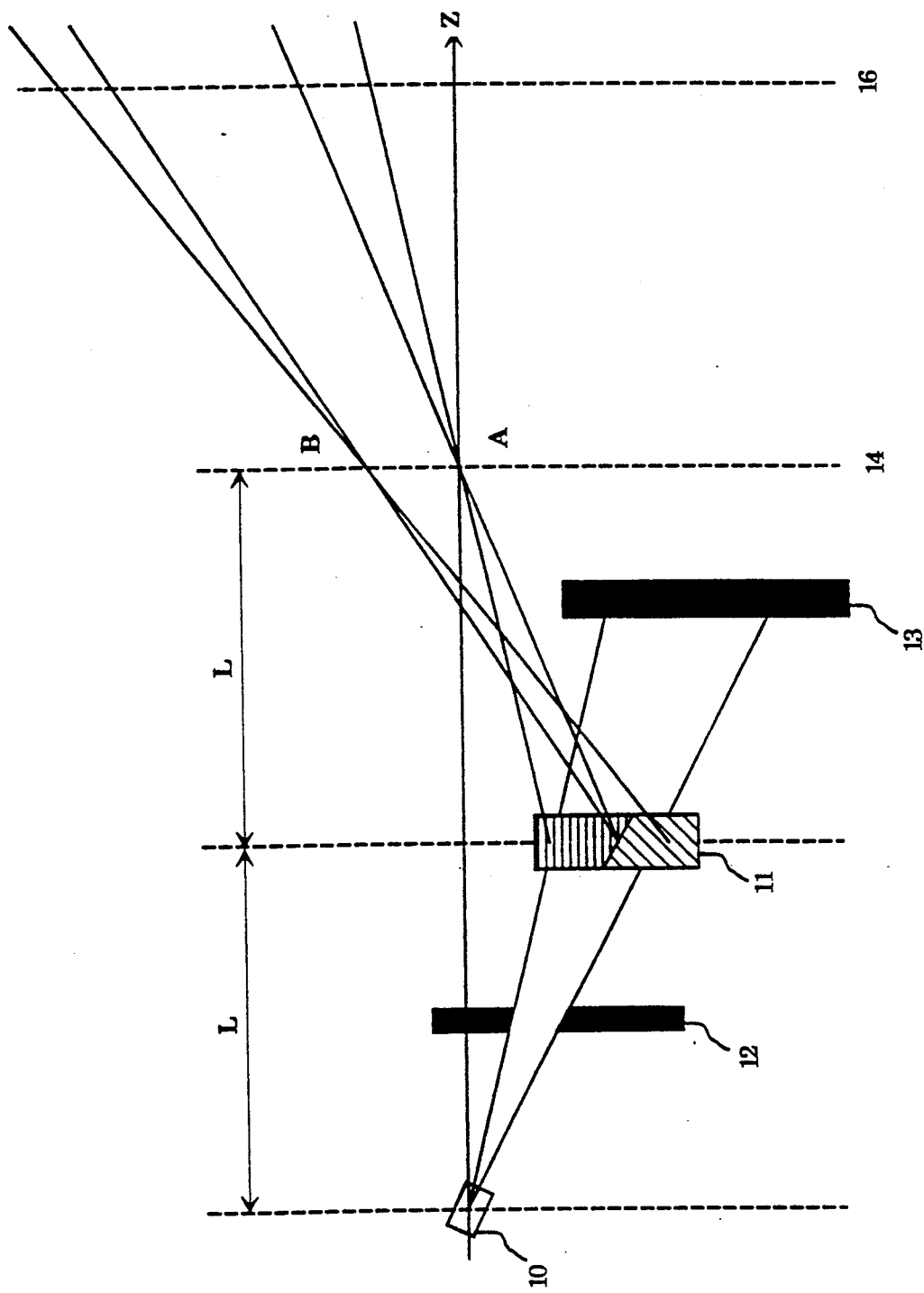

FIGS. 2a and 2b schematically show, respectively a perspective and a projection view, of an assembly according to the invention using an X-ray generator 10 of the previously described type. At the position of this generator a coordinate system Oxyz is traced, direction Oz substantially corresponding to the propagation direction and being more clearly defined in FIG. 2b. The part to be analyzed 11 extends perpendicularly to the plane of FIG. 2b (zOy) and is placed at half distance between the focus of the generator and a so-called focusing plane 14. A diaphragm 12, with horizontal and vertical openings, defines a maximum illuminated surface compatible with the physical laws of diffraction (energy of the generator, generator part distance, dimensions of the part ...). The so analyzed surface can attain more than one square centimeter.

The observation is carried out by a camera (or other detector) generally placed in the focusing plane at a distance 2L of the focus of the generator.

The above mentioned distances L will be chosen as a function of the considered problems and can be, for example, comprised between 50 cm and 2 m; these values constitute an order of magnitude and are not restrictive.

A screen 13 can be used, such as represented in FIG. 2b, to stop the X-rays passing through the part without deviation. Without this screen, it is possible to observe the direct radiation in zone 21 or 22 to determine whether the part has structural defects such as bubbles (represented as circles in FIG. 2a).

The observation and immediate analysis of the diffracted radiation are principally carried out with an X-ray camera; but a finer analysis can be done if necessary by placing an X-ray detector (mono or bi-dimensional) in the focusing plane. A movement of this detector in the y-direction, associated to an intensity profile analysis, provides accurate information on the disorientation and the mosaics parameters.

What has been described up to now is essentially what happens in the focusing plane 14 which was considered as the observation plane.

It is clear for those skilled in the art that the observation can be carried out in a plane 16, called image plane, more distant from the part. In this plane an image forms itself, associated to each of the crystalline defects of the part.

If the part effectively has a plurality of crystallographically disoriented grains, as many images as there are grains will be formed.

These images can eventually superimpose. The use of a diaphragm (not represented) placed in the focal plane allows to isolate them by selecting associated diffraction lines.

Each image represents a view by transmission of the diffracting crystalline zone; this view is deformed due to different enlargement factors:

the enlargement factor parallel to axis ox equals:

$$G_{ox} = d_{image}/L,$$

the enlargement factor parallel to axis oy equals:

$$G_{oy} = (d_{image} - 2L)/L,$$

where $d_{image}$ is equal to the distance between the image plane and the focus of the generator, and L is equal to the distance between the part and the focus of the generator.

This geometrical deformation can be corrected by image processing.

If part 11 is monocrystalline and if a network of oriented crystalline planes exist satisfying the Bragg relation for a range of wave lengths among the wave lengths emitted in the spectrum, then the whole considered crystalline zone diffracts a radiation which refocuses in one line A situated in the focusing plane 14.

If the part is perfectly monocrystalline, and only in the case where the X-ray generator has an effectively punctual focus, an image in the form of a fine line is obtained in plane 14.

The length of this line is defined by the double of the dimension of the illuminated portion of the part in the Ox direction; its width is equal to the dimension of the focus (a few tenths of a mm) when the part is of small thickness (<1 cm).

Hereabove, it has been supposed that the spectral width of the source was sufficient for each concerned reticular plane to be in the Bragg condition with respect to one of the wave lengths emitted by the source. Those skilled in the art will note that this implies that conditions must be satisfied with respect to the relation between the spectral width $\Delta\lambda$ of the source, the Bragg angle $\theta$, and the opening of the beam emitted by the generator. These relations will be developed by referring to FIG. 3.

Figure 3:
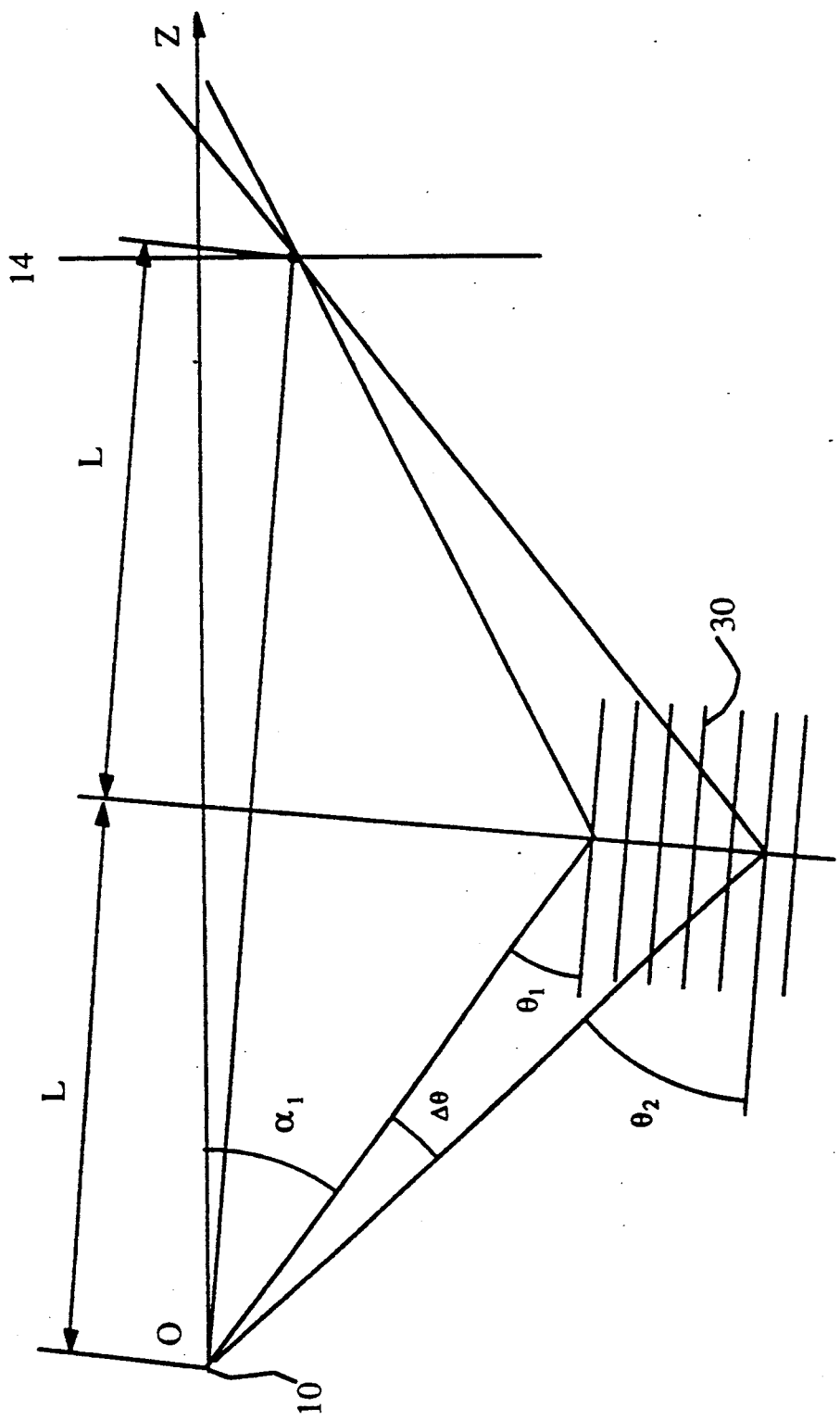
FIG. 3 explicits the notations relative to the X-ray diffraction in the monocrystalline part.

In FIG. 3, it is supposed that the part to be analyzed has previously been pre-oriented so that its reticular planes 30 diffract the beam substantially at the center of the detector.

The reference system Oxyz will thus be oriented so that axis Oz passes through the center of the detector.

$\Delta\theta$ is the opening of the beam illuminating part 11 from the X-ray generator;

$\theta_1$ is the Bragg angle corresponding to an end of the illuminated surface of the part and $\theta_2$ the Bragg angle corresponding to the other end.

In the assumption of a pre-orientation of the crystal (diffracted beam substantially at the center of the detector) the angle $\alpha_1$ between the minimum incident ray and axis Oz is substantially equal to $\theta_1$.

In order to obtain a diffraction, the generator must produce an X-ray beam of sufficient spectral width so that the Bragg relation $\lambda = 2 \cdot d \cdot \sin \theta$ between the wave length $\lambda$ of the X radiation, the angle $\theta$ and the lattice parameter d is satisfied for any angle $\theta$ comprised between $\theta_1$ and $\theta_2$.

This spectral width can be obtained by derivation of the Bragg relation:

$$\Delta\lambda = 2d \cdot \Delta\theta \cdot \cos \theta.$$

Considering the used energies, the angles $\theta$ are small; $\cos \theta$ is thus substantially equal to 1 and the spectral width of the source $\Delta\lambda$ must satisfy the relation:

$$\Delta\lambda = 2d(\theta_2 - \theta_1).$$

Practically, the reticular distances are generally comprised between 1 and 3 Angströms (0.1 and 0.3 nm). For d=2 Å, this leads to the relation $\Delta\lambda$ (Å)=$4\Delta\theta$ (radians). If $x_0$ is the width of the part and L the distance between the generator and the part, for a value $x_0 = 3$ cm and a value L=200 cm, it will be necessary in this particular case, that the spectral width of source $\Delta\lambda$ be equal to: $\Delta\lambda = 4 \times 3/200 = 0.06$ Å, which is compatible with the considered spectral width in FIG. 1.

It must be noted that the invention allows $\lambda$ and $\Delta\lambda$ to be varied in a particularly simple way by modifying the value of the high voltage of the generator (see FIG. 1). The average wave length can also be chosen by shifting the part parallel to axis Oy (this changes the values of angles $\theta$).

The images are obtained by converting the X radiation in an optical image visible by an X-ray camera provided with an image intensifier or by a bi-dimensional detector. The detection must have a very good spatial resolution (<0.5 mm), a high sensitivity, and a good homogeneous response on the entire surface of the detector; its active surface will have to be of a few square centimeters.

FIGS. 2a and 2b show by hatches that part 11 comprises two crystallographically distinct zones. As a result, two images A and B are formed in the focal plane 14.

Figure 4A:
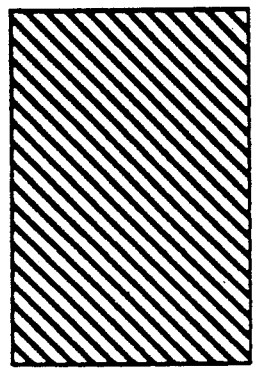
FIGS. 4a, 4b and 4c show examples of observations carried out with the assembly according to the invention and relative to different crystalline defects.
Figure 4A:
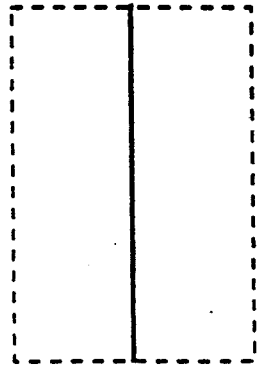
Figure 4B:
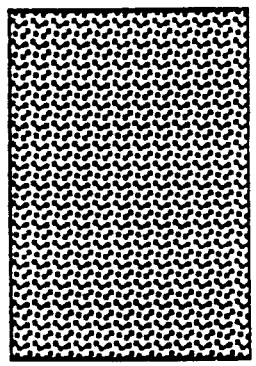
Figure 4B:
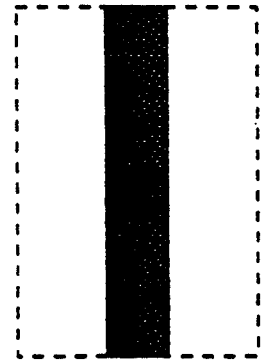
Figure 4C:
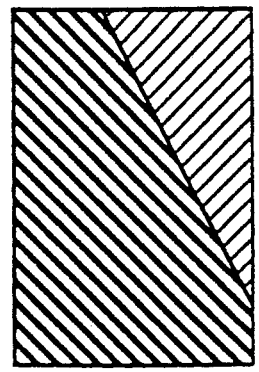
Figure 4C:
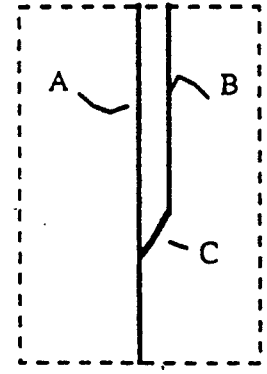

A more detailed example of different defects which can be encountered is shown by FIGS. 4a to 4c, in each of which the left represents the studied structure and the right represents the corresponding observed image in the focusing plane.

In FIG. 4a, the part is a perfect crystal;

In FIG. 4b, the crystal is of an homogeneous mosaic type;

In FIG. 4c, the crystal has two slightly disoriented grains; the distance between the two lines A and B allows the calculation of the disorientation of the grains. If the change of orientation is not abrupt, a transition zone C between lines A and B appears.

We claim:

1. An X-ray volume analysis method of detecting crystalline defects of an object, comprising the steps of:
   positioning the object in a plane situated equidistant from the focus of a point source of X-rays and a focusing plane;
   illuminating the object using said point source of X-rays using a beam having a band width $\Delta\lambda$ and a predetermined angular opening $\Delta\theta$, the opening $\Delta\theta$ of the beam being defined by $\Delta\theta \leq \Delta\lambda/2d\cdot\cos\theta$, d being an interreticular distance for predetermined reticular planes;
   orienting the object to obtain the diffraction on a chosen family of the reticular planes; and
   collecting and analyzing the X-ray beam near the focusing plane.

2. The method as claimed in claim 1, wherein the steps of collecting and analyzing comprises the steps of
   isolating observed spots in the focusing plane using diaphragms; and
   collecting and analyzing images transmitted beyond the focusing plane.

3. The method as claimed in claim 1, wherein a diverging beam from a point focus is directed through an aperture positioned between the source of X-rays and the object so that the beam substantially illuminates the whole object.

4. The method as claimed in claim 1, wherein the source of X-rays provides a radiation of an energy greater than 100 kev.

5. The method as claimed in claim 1, wherein the object is a monocrystal.

6. The method as claimed in claim 1, wherein said illuminating step illuminates said object using a polychromatic beam having a predetermined spectral width.

7. A method for detecting crystalline defects of a specimen, comprising the steps of:
   positioning the specimen in a plane situated substantially equidistant from the focus of an X-ray source and a focusing plane;
   concurrently irradiating a whole of a surface of said specimen with said X-ray source using a beam having a bandwidth $\Delta\lambda$ and a predetermined angular divergence defined by $\Delta\theta \leq \Delta\lambda/2d\cdot\cos\theta$, d being an interreticular distance for predetermined reticular planes;
   orienting the specimen to obtain the diffraction on a chosen family of the reticular planes; and
   collecting and analyzing the X-ray beam proximate the focusing plane.

8. The method according to claim 7, wherein said irradiating step includes irradiating the whole of the surface of said specimen with said X-ray source using a polychromatic beam.

9. The method according to claim 7, wherein the steps of collecting and analyzing comprises the steps of:
   isolating observed spots in the focusing plane using diaphragms; and
   collecting and analyzing images transmitted beyond the focusing plane.

10. The method according to claim 7, wherein said X-ray source comprises a point source of X-rays which are directed through an aperture positioned between the X-ray source and the specimen whereby the X-ray beam substantially illuminates the whole of said surface of said specimen.

11. The method according to claim 7, wherein the X-ray source emits X-rays having an energy greater than 100 kev.

12. An apparatus for detecting crystalline defects of a specimen, comprising:
    a source of a beam of X-rays having a bandwidth $\Delta\lambda$ and a predetermined angular divergence defined by $\Delta\theta \leq \Delta\lambda/2d\cdot\cos\theta$, d being an interreticular distance for predetermined reticular planes;
    means for positioning the specimen in a plane situated substantially equidistant from the focus of the polychromatic source and a focusing plane;
    means for orienting the specimen to obtain the diffraction on a chosen family of the reticular planes; and
    means for collecting and analyzing the X-ray beam proximate the focusing plane.

13. The apparatus according to claim 12, wherein said source of a beam of X-rays is a polychromatic source of x-rays.

14. The apparatus according to claim 12, wherein the means for collecting and analyzing comprises:
    means for isolating observed spots in the focusing plane using diaphragms; and
    means for collecting and analyzing images transmitted beyond the focusing plane.

15. The apparatus of claim 12, wherein said source comprises:
    a point source of X-rays; and
    an aperture positioned between the source of X-ray and the specimen whereby the X-ray beam substantially illuminates the whole of said surface of said specimen.

16. The apparatus according to claim 14 wherein said point source of X-rays generates X-rays having an energy greater than 100 kev.

17. The apparatus according to claim 12 wherein said means for positioning the specimen includes means for positioning a turbine blade substantially equidistant from the focus of the source and said focusing plane.

* * * * *